(12) United States Patent
Lin et al.

(10) Patent No.: US 8,816,139 B2
(45) Date of Patent: Aug. 26, 2014

(54) FACILE AND EFFECTIVE METHOD OF PREPARING 1,4-BIS(CHLORODIFLUOROMETHYL)BENZENE

(75) Inventors: Chun Hsu Lin, Taipei (TW); Hung Cheng Yin, Keelung (TW); Chien Yi Sun, Kaohsiung (TW); Yung Yu Yin, Pingtung County (TW); Chuan Yu Chou, Taoyuan County (TW)

(73) Assignees: Yuan-Shin Materials Technology Corp., Taipei (TW); Chung-Shan Institute of Science and Technology, Armaments Bureau, M.N.D., Taoyuan County (TW)

( * ) Notice: Subject to any disclaimer, the term of this patent is extended or adjusted under 35 U.S.C. 154(b) by 0 days.

(21) Appl. No.: 13/477,188

(22) Filed: May 22, 2012

(65) Prior Publication Data
US 2013/0116482 A1    May 9, 2013

(30) Foreign Application Priority Data
Nov. 9, 2011   (TW) ................ 10140940 A

(51) Int. Cl.
   *C07C 17/14*    (2006.01)
   *C07C 22/08*    (2006.01)
(52) U.S. Cl.
   CPC ....................... *C07C 17/14* (2013.01)
   USPC ........................................................ 570/144
(58) Field of Classification Search
   None
   See application file for complete search history.

(56) References Cited

U.S. PATENT DOCUMENTS

| | | |
|---|---|---|
| 5,210,341 A | 5/1993 | Dolbier, Jr. |
| 5,841,005 A | 11/1998 | Dolbier, Jr. et al. |
| 6,150,499 A | 11/2000 | Dolbier, Jr. et al. |
| 6,284,933 B1 | 9/2001 | Dolbier, Jr. et al. |
| 7,868,213 B2 * | 1/2011 | Chou et al. .................. 570/145 |

FOREIGN PATENT DOCUMENTS

| | | | |
|---|---|---|---|
| JP | H05255149 A | | 10/1993 |
| JP | 2000-281599 A | | 10/2000 |
| JP | 2000281599 A | * | 10/2000 |
| JP | 2001515507 A | | 9/2001 |
| JP | 2009161530 A | | 7/2009 |

OTHER PUBLICATIONS

Chow, A. W. et al. Journal of Organic Chemistry 1970, 35, 20-22.*
S.W.Chow, L.A.Pilato, W.L.Wheelwright, The Synthesis of 1,1,2,2,9,9,10,10-Octafluoro[2.2]paracyclopane, The Journal of Organic Chemistry, 1970, p. 20-22, 35.

* cited by examiner

Primary Examiner — Jafar Parsa
Assistant Examiner — Medhanit Bahta
(74) Attorney, Agent, or Firm — Bacon & Thomas, PLLC

(57) ABSTRACT

The present invention relates to a facile method of preparing 1,4-bis(chlorodifluoromethyl)benzene, comprising the steps of: (A) providing a reactant liquid of 1,4-bis(difluoromethyl)benzene; optionally (B) providing a light source for UV radiation; and (C) introducing chlorine gas into the reactant liquid at a temperature of 50-90° C. under a pressure above 1 atm to obtain 1,4-Bis(chlorodifluoromethyl)benzene. The invented facile method can be utilized in a batch process or a continuous process for effective production of 1,4-bis(chlorodifluoromethyl)benzene.

16 Claims, 2 Drawing Sheets

FACILE AND EFFECTIVE METHOD OF PREPARING 1,4-BIS(CHLORODIFLUOROMETHYL)BENZENE

CROSS REFERENCE TO RELATED APPLICATION

This application claims the benefits of the Taiwan Patent Application Serial Number 100140940, tiled on Nov. 9, 2011, the subject matter of which is incorporated herein by reference.

BACKGROUND OF THE INVENTION

1. Field of the Invention

The present invention relates to a method of synthesizing 1,4-bis(chlorodifluoromethyl)benzene). More particularly, the present invention relates to a method of synthesizing 1,4-bis(chlorodifluoromethyl)benzene) in a high yield by using a batch process or a continuous process, which has simple processes and short reaction time.

2. Description of Related Art

By chemical vapor deposition (CND) processes in vacuum pyrolysis, parylene polymers can be formed into ultra-thin films, which have many excellent properties such as electrical property, heat resistance, chemical stability, high transparency, etc. Accordingly, parylene polymers have been commonly used in thin films and coatings and widely applied in many areas such as electrical isolation in printed circuit boards, moisture proofing in sensors or medical equipment, electrical insulation in electronic devices, protective coatings, packaging materials, anticorrosion for metal coating, etc.

Currently, fluorinated parylene such as poly(tetrafluoro-p-xylene) represented by the following formula (1) has been applied to dielectric films used in electronics and coating industries owing to its high boiling point, low-dielectric constant, and good anti-ultraviolet and anti-aging properties.

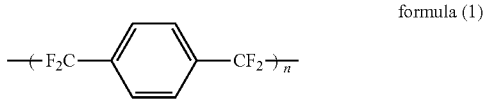

formula (1)

Presently, a method of coating with fluorinated parylenes is to polymerize active monomers on the surface of an object. Unlike the general steps of liquid coating process, this coating process is executed as follows: heating and vaporizing fluorinated para-xylene dimers such as octafluoro-(2,2)-paracyclophane (AF4) represented by the following formula (2), converting the dimers into free radicals of fluorinated para-xylene monomers by prolysis, and then polymerizing the monomers on the object to form poly(tetrafluoro-p-xylene), which is called parylene FIT represented by formula (1).

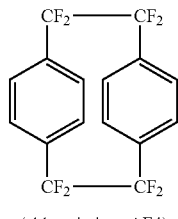

(abbreviation: AF4)

formula (2)

1,4-bis(chlorodifluoromethyl)benzene (CFB) represented by the following formula (3) is an important precursor for preparing fluorinated parylene dimmers (AF4).

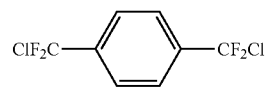

formula (3)

A conventional method of preparing 1,4-bis(chlorodifluoromethyl)benzene comprises the following steps: dissolving 1,4-bis(difluoromethypbenzene in a solvent such as carbon tetrachloride ($CCl_4$) to form a reactant solution; providing a photo initiator and introducing chlorine gas into the reactant solution; and initiating the reaction by light irradiation under the catalysis of the photoinitiator so as to obtain 1,4-bis(chlorodifluoromethyl)benzene. However, the method has several disadvantages in that: (1) long reaction time; (2) low yield; (3) addition of a photoinitiator or a solvent such as $CCl_4$ is required, which is not eco-friendly; (4) complex processes for purification; and (5) consuming high amounts of energy to obtain products.

Therefore, it is desirable to provide a rapid, simple and low cost method of synthesizing 1,4-bis(chlorodifluoromethyebenzene for mass production. The present invention provides a simple, low cost method of synthesizing 1,4-bis(chlorodifluoromethyl)benzene used as an important precursor for preparing fluorinated para-xylene dimers,

SUMMARY OF THE INVENTION

The object of the present invention is to provide a method of synthesizing 1,4-bis(chlorodifluoromethyl)benzene (CFB), as represented by the following reaction (I):

reaction (I)

$$\underset{\underset{CF_2H}{|}}{\overset{\overset{CF_2H}{|}}{\bigcirc}} \xrightarrow{\underset{UV}{Cl_2}} \underset{\underset{CF_2Cl}{|}}{\overset{\overset{CF_2Cl}{|}}{\bigcirc}}$$

(abbreviation: TFPX)        (abbreviation: CFB)

The present invention provides a method of synthesizing 1,4-bis(chlorodifluoromethyl)benzene (CFB), comprising the steps of: (A) providing a reactant liquid 1,4-bis(difluoromethyl)benzene (TFPX); and (B) introducing chlorine gas ($Cl_2$) to the reactant liquid at a temperature of 50-90° C. under a pressure above 1 atm to obtain 1,4-bis(chlorodifluoromethyl)benzene.

In the method of the present invention, 1,4-bis(difluoromethyl)benzene can directly react with $Cl_2$ under pressure slightly higher than 1 atm. The method of the present invention can omit the step of dissolving 1,4-bis(difluoromethyl)benzene into a solvent and initiate the reaction between 1,4-bis(difluoromethyl)benzene and chlorine gas by light irradiation without using any photoinitiator. Since the reactant of 1,4-bis(difluoromethyl)benzene can be used as a solvent and completely reacted, the step of removing the solvent can be omitted. Meanwhile, the purification process for removing the photoinitiator also can be omitted due to no photoinitiator being used in the method of the present invention. Therefore, the present invention provides a simple, rapid, and low cost method to prepare 1,4-bis(chlorodifluoromethyl)benzene for mass production. More particularly, the method of the present invention provides a raw material, 1,4-bis(chlorodifluoromethyl)benzene, which can be a precursor for a process of preparing poly(tetrafluoro-p-xylene).

In the method of the present invention, the reaction is preferably performed at enclosed space and kept at a pressure above 1 atm. By maintaining the pressure above 1 atm, the chlorine gas can be dissolved in 1,4-bis(difluoromethyl)benzene. Moreover, the chlorine gas can react with 1,4-bis(difluoromethyl)benzene without any solvent.

In addition, in the method of the present invention, the equivalent of chlorine gas preferably is more than the equivalent of 1,4-bis(difluoromethyl)benzene, so as to keep the pressure above 1 atm during the reaction. A molar ratio of chlorine gas to 1,4-bis(difluoromethyl)benzene may be in a range of 2:1 to 4:1, and preferably in a range of 2.2:1 to 3:1. If the molar ratio of chlorine gas to 1,4-bis(difluoromethyl) benzene is less than 2:1, the pressure of chlorine gas during the reaction is relatively low so that the reaction rate is decreased, the reaction time is increased, and the reaction can not be performed completely. If the molar ratio of chlorine gas to 1,4-bis(difluoromethyl)benzene is more than 4:1, the pressure of chlorine gas during the reaction is excessively high so as to increase the concentration of reaction byproduct (e.g. HCl) which suppresses the reaction to cause an incomplete reaction. Herein, the step (B) can further comprise a step of neutralizing the unreacted chlorine gas by using an alkaline solution such as KOH, NaOH, or $NH_4OH$ solution. In the method of the present invention, the reaction pressure of the method can be in a range of 1.001 to 1.10 atm. If the pressure is less than 1 atm, the reaction system of the present invention is presented as negative pressure so that chlorine gas can not he sufficiently dissolved in 1,4-bis(difluoromethyl)benzene. If the pressure is higher than 1.10 atm, the concentration of HCl formed from the reaction is relatively high so as to suppress the reaction and cause an incomplete reaction Furthermore, in the method of the present invention, the step (B) may optionally comprise a step of irradiating the reactant liquid by a light source, so as to increase the reaction rate, shorten the reaction time, and facilitate mass production. The light source may provide a UV light. The light source for providing UV light is not particularly limited, and may be a conventional light apparatus (e.g. an ultraviolet lamp or a mercury-vapor lamp) known in the art. No matter if the ultraviolet lamp or the mercury-vapor lamp is used, the reaction temperature can be changed by the intensity of the light source. In addition, in order to react completely, the reaction time can also be adjusted according to forms, intensities, and reaction temperatures of the light sources.

According to one aspect of the method of the present invention, the light source may he an ultraviolet lamp. The ultraviolet lamp can provide UV light in an intensity range of 10 to 400 W, and preferably is 30 to 90 W.

Furthermore, the reaction temperature may be in a range of 30 to 100° C., and preferably is 70 to 90° C.

According to another aspect of the method of the present invention, the light source may be a mercury-vapor lamp. The mercury-vapor lamp can provide UV light in an intensity range of 300 to 1000 W, and preferably is 350 to 450 W. Furthermore, the reaction temperature may be in a range of 30 to 80° C., and preferably is 50 to 70 ° C.

As described above, by the facile method of synthesizing 1,4-bis(chlorodifluoromethyl)benzene according to the present invention, the reaction time can be shortened, the steps of the method can be simplified, and the yield of 1,4-bis(chlorodifluoromethyl)benzene can be raised. in addition, in the present invention, 1,4-bis(chlorodifluoromethyl)benzene can be prepared for mass production and applied during the process of preparing Octafluoro-[2,2]paracyclophane (AF4) by related industries.

Additionally, the present invention also provides a reaction system for a continuous process of synthesizing 1,4-bis(chlorodifluoromethyl)benzene, comprising: a raw material tank receiving 1,4-bis(difluoromethyl)benzene; a chlorine supplying element providing a chlorinating agent; a reactor connecting with the raw material tank and the chlorine supplying element, wherein the 1,4-bis(chlorodifluoromethyl)benzene received in the raw material tank enters the reactor through a connecting line, and the chlorinating agent provided from the chlorine supplying element enters the reactor; an absorber connecting with the reactor and an alkaline solution supplying element, wherein the alkaline solution supplying element provides an alkaline solution to the absorber; and a separating apparatus for separating 1,4-bis(chlorodifluoromethyl)benzene.

In the reaction system for the continuous process in the present invention, the chlorinating agent preferably is chlorine gas.

Herein, the alkaline solution in the absorber is used to neutralize the unreacted chlorine gas. In addition, the reaction system for the continuous process can further comprise a neutralizer tank, which is connected with the reactor and the separating apparatus through a connecting line. Furthermore, the neutralizer tank is also connected with the alkaline solution supplying element, wherein the alkaline solution supplying element provides the alkaline solution to the neutralizer tank. The alkaline solution supplying element can further provide the absorber under a pressure, which can be a back pressure to the reactor so as to keep the pressure in the reactor above 1 atm.

Furthermore, in the reaction system for the continuous process in the present invention, the separating apparatus can comprise a separation chamber and at least one distillation column, which are connected with the reactor by connecting lines. The separation chamber connects with distillation columns by connecting lines. By using the separating apparatus to purify the product of the reaction, 1,4-bis(chlorodifluoromethyl)benzene with a high-purity can be obtained.

Other objects, advantages, and novel features of the invention will become more apparent from the following detailed description when taken in conjunction with the accompanying drawings.

DETAILED DESCRIPTION OF THE PREFERRED EMBODIMENT

Herein below, the present invention will be described in detail with reference to the embodiments. The present invention may, however, be embodied in many different forms and should not be construed as being limited to the embodiments set forth herein. Rather, these embodiments are provided to fully convey the concept of the invention to those skilled in the art.

The method of synthesizing 1,4-bis(chlorodifluoromethyl) benzene (hereinafter "CFB") in the present invention is performed by using a reaction system for a batch process or a continuous process.

Figure 1:
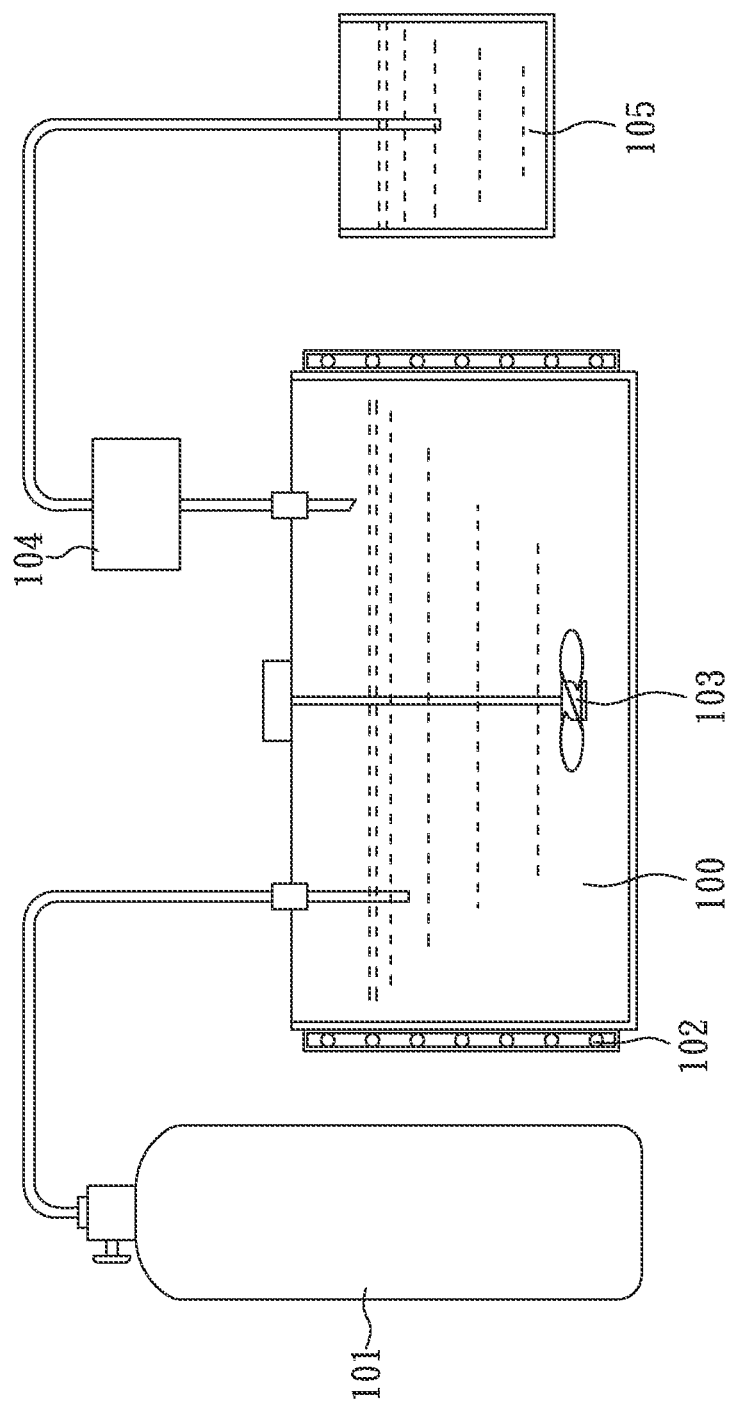
FIG. 1 shows a schematic diagram of a reaction system for a batch process according to the present invention.

Referring to FIG. 1, a schematic diagram of a reaction system for a batch process according to the present invention is shown. At first, 1,4-bis(difluoromethyl)benzene (hereinafter "TFPX") received in a reaction tank (100) is heated by a heater (102), and then chlorine gas from a cylinder (101) is introduced into the reaction tank (100) with continuous stirring by a stirrer (103) to synthesize 1,4-bis(chlorodifluoromethyl)benzene. Meanwhile, the unreacted chlorine gas passes through a condenser (104) to a neutralizer tank (105) to be neutralized. Herein, the reaction system stays under slightly positive pressure so as to maintain the solubility of chlorine gas. In lieu of using the heater (102), the reaction solution can also be heated by hot water (jacket heating).

In addition, the reaction system for the batch process can further provide a light source (it is not shown in FIGs) under the reaction tank (100) to irradiate the reaction mixture, which can enhance the reaction rate.

Figure 2:
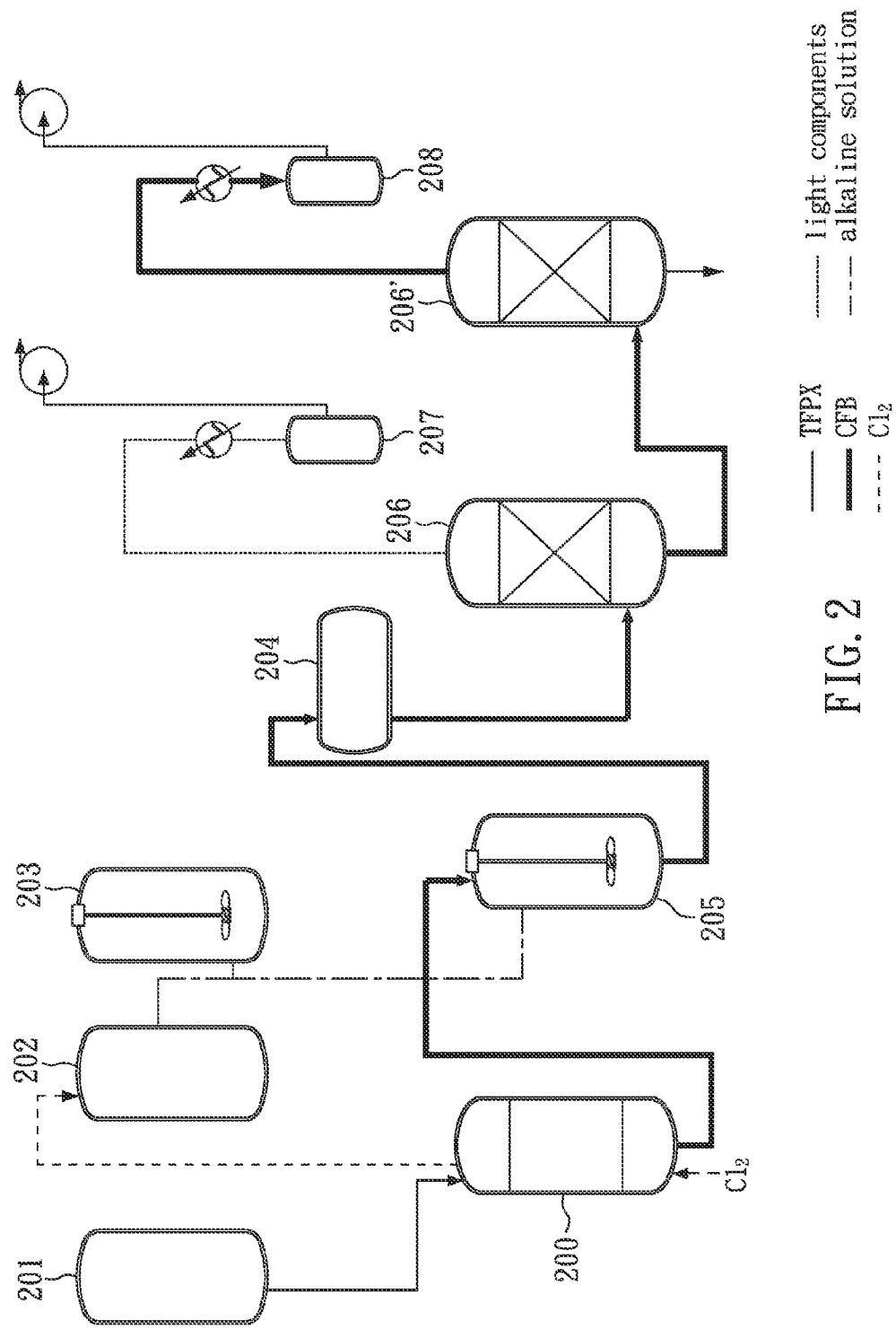
FIG. 2 shows a schematic diagram of a reaction system for a continuous process according to the present invention.

Furthermore, referring to FIG. 2, a schematic diagram of a reaction system for a continuous process according to the present invention is shown. TFPX is provided from a raw material tank (201) into a reactor (200). Meanwhile, $Cl_2$ is introduced into the reactor (200) by a chlorine supplying element (e.g. $Cl_2$ cylinder) so that chlorine gas is reacted with TFPX in the reactor (200). The unreacted chlorine gas is introduced. from the top of the reactor to an absorber (202). By providing a solution of NaOH into the absorber (202) from an alkaline solution supplying element (203), the unreacted chlorine gas can he absorbed. Upon completion of the reaction, the reaction mixture flows into a neutralizer tank (205) to be neutralized with the solution of NaOH provided from the alkaline solution supplying element (203). The reaction mixture having crude CFB is obtained after neutralization and then introduced into a separation chamber (204) to perform oil-water phase separation. The oil phase enters a first distillation column (206) to separate light components from the mixture by vacuum distillation, and the light components from the top of the first distillation column (206) are stored in a light component collector (207).

Then, crude CFB without light components is introduced into a second distillation column (206') to separate the product of CFB by vacuum distillation. The product of CFB from the top of the second distillation column (206') can be collected in a product collector (208). In this case, the reaction system for the continuous process stays under slightly positive pressure so as to maintain a suitable solubility of chlorine gas. In addition, the method of the present invention may further comprise a step of providing a light source (it is not shown in FIGs) to enhance the reaction rate.

In addition to using a reaction system for a batch process, the method of the present invention can also be performed by a reaction system for a continuous process for mass production of CFB in industries.

According to an embodiment of the present invention, the method of synthesizing CFB will become more apparent from the following detailed description. Herein, the following Examples and Comparative Examples are performed to synthesize CFB by a reaction system for a batch process or a continuous process as described above.

EXAMPLE 1

First, 300 g (1.69 mole) of TFPX is added into a glass reactor and stirred evenly by a stirrer. Subsequently, TFPX in the glass reactor is heated to 60° C., by hot water (jacket heating) and irradiated with a mercury-vapor lamp (400 W).

At this time, slightly excessive (about 336 g; 4.73 mole) is continuously introduced into the glass reactor so as to perform chlorination. During the reaction the pressure in the glass reactor is kept slightly higher than 1 atm (about 1.01 atm), and the reaction is maintained for 45 minutes to obtain a light yellow liquid. Then, the light yellow liquid (GC purity: 99.32%) is neutralized by an alkaline solution and treated with oil-water phase separation, followed by distillation under a pressure of 10 torr at 125° C. (corresponding to the boiling point of CFB) to obtain 408 g of colorless liquid product in a yield of 98.1%.

Finally, the liquid product as described above is analyzed by GC. According to the results of GC analysis, the formation of CFB is confirmed, and the purity of CFB is 99.59%. Furthermore, the liquid product is analyzed by GC/MS. The results of analysis for the product are shown as follows: the molecular weight: 247 g/mol ($C_8H_4Cl_2F_4$); $F^{19}$ NMR: $\delta_{CFCl3}$-50.1 ppm (s); and $H^1$NMR: $\delta_{TMS}$ 7.8 ppm (s).

EXAMPLE 2

First, 600.01 g (3.37 mole) of TFPX is added into a glass reactor and stirred evenly by a stirrer. Subsequently, TFPX in the glass reactor is heated to 60° C. by hot water (jacket heating) and irradiated with a mercury-vapor lamp (400 W).

At this time, slightly excessive $Cl_2$ (about 600 g; 8.43 mole) is continuously introduced into the glass reactor so as to perform chlorination. During the reaction the pressure in the glass reactor is kept slightly higher than 1 atm (about 1.01 atm), and the reaction is maintained for 100 minutes to obtain a light yellow liquid.

After the steps as described above, the light yellow liquid is analyzed by GC. According to the results of GC analysis, the formation of CFB is confirmed, and the purity of CFB is 99.49%.

EXAMPLE 3

First, 441.90 g (2.48 mole) of TFPX is added into a glass reactor and stirred evenly by a stirrer. Subsequently, TFPX in the glass reactor is heated to 75° C. by hot water (jacket heating) and irradiated with two ultraviolet lamps (Both are 36 W).

At this time, slightly excessive $Cl_2$ (about 580 g; 8.18 mole) is continuously introduced into the glass reactor so as to perform chlorination. During the reaction the pressure in the glass reactor is kept slightly higher than 1 atm (about 1.01 atm), and the reaction is maintained for 95 minutes to obtain a light yellow liquid.

After the steps as described above, the light yellow liquid is analyzed by GC. According to the results of GC analysis, the formation of CFB is confirmed, and the purity if CFB is 99.44%.

EXAMPLE 4

First, 441.78 g (2.48 mole) of TFPX is added into a glass reactor and stirred evenly by a stirrer. Subsequently, TFPX in the glass reactor is heated to 80° C. by hot water (jacket heating) and irradiated with an ultraviolet lamp (36 W).

At this time, slightly excessive $Cl_2$ (about 475 g; 6.60 mole) is continuously introduced nub the glass reactor so as to perform chlorination.

During the reaction the pressure in the glass reactor is kept slightly higher than 1 atm (about 1.01 atm), and the reaction is maintained for 110 minutes to obtain a light yellow liquid.

After the steps as described above, the light yellow liquid is analyzed by GC. According to the results of GC analysis, the formation of CFB is confirmed, and the purity of CFB is 99.46%.

EXAMPLE 5

First, 100.00 g (0.56 mole) of TFPX is added into a glass reactor and stirred evenly by a stirrer. Subsequently, TFPX in the glass reactor is heated to 80° C. by hot water (jacket heating).

At this time, slightly excessive $Cl_2$ (about 112 g; 1.55 mole continuously introduced into the glass reactor so as to perform chlorination. During the reaction the pressure in the glass reactor is kept slightly higher than 1 atm (about 1.01 atm), and the reaction is maintained for 3.5 hours to obtain a light yellow liquid.

After the steps as described above, the light yellow liquid is analyzed by GC. According to the results of GC analysis, the formation of CFB is confirmed, and the purity of CFB is 99.78%. Thus, the result shows the method of synthesizing CFB according to the present invention can be performed without adding any photoinitiator or UV irradiation. By increasing the reaction time, the chlorination reaction can be successfully performed.

EXAMPLE 6

TFPX, which is preheated to 80° C., is continuously introduced into a reactor through the top of the reactor by using a peristaltic pump at a rate of 1 Kg/Hr. When half height of the reactor is filled with TFPX, chlorine gas is introduced at a rate of 13-15 g/min, and the reactor is irradiated with an ultraviolet lamp. After about 2 hours, the reactor is almost full of a light yellow liquid. At this time, a discharging valve of the reactor is opened to discharge the reaction liquid at a predetermined rate and maintain the liquid level of the reactor at a particular height.

Finally, the light yellow liquid is led to a neutralizer tank and neutralized with an alkaline solution provided from an alkaline solution supplying element. After being neutralized, the reaction liquid is introduced into a separation chamber to perform oil-water phase separation.

The mixture of oil phase is introduced into a distillation tank to remove light components at a first distillation stage and heavy components at a second distillation stage. Eventually, a colorless liquid product is obtained in a product collector.

Furthermore, the colorless liquid product in the product collector is analyzed by GC. According to the results of GC analysis, the formation of CFB is confirmed, and the purity of CFB is 99.35%.

After that, the peristaltic pump keeps working as described above, the colorless liquid product of CFB is taken out from the product collector after 5 hours and analyzed by GC, and its purity is 99.47%. After 10 hours, the colorless liquid product is taken out from the product collector again and analyzed by GC, and its purity is 99.61%.

After feeding 10.13 Kg of TFPX, 13.72 Kg of the colorless liquid product is obtained, and the yield is 97.6%. According to the results of GC analysis, the formation of CFB is confirmed, and the purity of CFB is 99.51%.

COMPARATIVE EXAMPLE 1

First, 350.53 g (1.97 mole) of TFPX and 0.57 g (0.003 mole) of 2,2'-azobis(2-methylpropionitrile) used as a photoinitiator are added into a glass reactor and stirred evenly by a stirrer. Subsequently, the reactant mixture in the glass reactor is heated to 60° C. by hot water (jacket heating) and irradiated with a mercury-vapor lamp (400 W).

At this time, slightly excessive $Cl_2$ (about 392 g; 5.52 mole) is continuously introduced into the glass reactor so as to perform chlorination. During the reaction the pressure in the glass reactor is kept slightly higher than 1 atm (about 1.01 atm), and the reaction is maintained for 50 minutes to obtain a light yellow liquid.

The light yellow liquid is neutralized, followed by oil-water phase separation. Next, the mixture of oil phase is distilled to eliminate light components and heavy components so as to obtain a colorless liquid of 444.3 g. According to the results of GC analysis, the formation of CFB is confirmed, and the purity and yield of CFB are 99.37% and 91.3%, respectively.

COMPARATIVE EXAMPLE 2

First, 300.27 g (1.69 mole) of TFPX and 480.40 g of carbon tetrachloride ($CCl_4$) are added into a glass reactor and stirred evenly by a stirrer. Subsequently, the reactant mixture in the glass reactor is heated to 60° C. by hot water (jacket heating) and irradiated with a mercury-vapor lamp (400 W).

At this time, $Cl_2$ (about 275 g; 3.89 mole) is continuously introduced into the glass reactor so as to perform chlorination. During the reaction the pressure in the glass reactor is kept slightly higher than 1 atm (about 1.01 atm), and the reaction is maintained or 6 hours to obtain a light yellow liquid.

The light yellow liquid is neutralized, followed by oil-water phase separation. Next, the mixture of oil phase is distilled to eliminate $CCl_4$, light components and heavy components so as to obtain a colorless liquid of 366.9 g. According the results of GC analysis, the formation of CFB is confirmed, and the purity and yield of CFB are 99.56% and 87.9%, respectively.

COMPARATIVE EXAMPLE 3

First, 302.50 g (1.70 mole) of TFPX and 480.72 g carbon tetrachloride ($CCl_4$) are added into a glass reactor and stirred evenly by a stirrer. Subsequently, the reactant mixture in the glass reactor is heated to 60° C. by hot water (jacket heating) and irradiated with a mercury-vapor lamp (400 W), At this time, $Cl_2$ (about 265 g; 3.74 mole) is continuously introduced into the glass reactor so as to perform chlorination.

During the reaction the pressure in the glass reactor is kept 1 atm, and the reaction is maintained for 15 hours to obtain a light yellow liquid.

After the steps as described above, the light yellow liquid is analyzed by GC. According to the results of GC analysis, the formation of CFB is confirmed, and the purity of CFB is 99.23%.

COMPARATIVE EXAMPLE 4

First, 300.19 g (1.69 mole) of TFPX and 480.12 g of carbon tetrachloride ($CCl_4$) are added into a glass reactor and stirred evenly by a stirrer. Subsequently, the reactant mixture in the glass reactor is heated to 60° C. by hot water (jacket heating) and irradiated with a mercury-vapor lamp (400 W).

At this time, slightly excessive $Cl_2$ (about 333 g, 4.39 mole) is continuously introduced into the glass reactor so as to perform chlorination. During the reaction the pressure in the glass reactor is kept slightly higher than 1 atm (about 1.01 atm), and the reaction is maintained for 1 hour to obtain a light yellow liquid.

After the steps as described above, the light yellow liquid is analyzed by GC. According to the results of GC analysis, the formation of CFB is confirmed, and the purity of CFB is 99.53%.

Comparing Example 1 with Comparative Example 1, it can be found that the method of the present invention can prepare high purity CFB in a short time period by heating or irradiation without using any photoinitiator.

In addition, compared to Comparative Examples 1-4 that use either a solvent or a photoinitiator in the preparation of high purity CFB, Examples 1-5 show that the method of the present invention can prepare high purity CFB without adding any photoinitiator or solvent. Therefore, the method provided by the present invention only requires a simple purification process and is suitable for mass production of CFB in rapid and low cost conditions. In addition, the method of the present invention does not need to add any solvent (e.g. $CCl_4$) or photo initiator during the reaction so as to reduce cost and protect the environment.

Furthermore, Example 6 shows that the method of the present invention can be performed by using a continuous process, which is suitable for mass production of CFB in simple and economical conditions.

Although the present invention has been explained in relation to its preferred embodiment, it is to be understood that many other possible modifications and variations can be made without departing from the spirit and scope of the invention as hereinafter claimed.

What is claimed is:

1. A method of synthesizing 1,4-bis(chlorodifluoromethyl)benzene, comprising the steps of:
    (A) providing a reactant liquid of 1,4-bis(difluoromethyl)benzene; and
    (B) introducing chlorine gas ($Cl_2$) into the reactant liquid at a temperature of 50-90° C. under a pressure in a range of 1.001 to 1.10 atm to obtain 1,4-bis(chlorodifluoromethyl)benzene wherein the step (B) further comprises a step of irradiating the reactant liquid by a light source.

2. The method according to claim 1, wherein the light source is an ultraviolet lamp.

3. The method according to claim 2, wherein the ultraviolet lamp provides light in an intensity range of 10 to 400 W.

4. The method according to claim 1, wherein the light source is a mercury-vapor lamp.

5. The method according to claim 4, wherein the mercury-vapor lamp provides light in an intensity range of 300 to 1000 W.

6. The method according to claim 1, wherein the molar ratio of chlorine gas to 1,4-bis(difluoromethyl)benzene is in a range of 2:1 to 4:1.

7. The method according to claim 1, wherein the step (B) further comprises a step of neutralizing the unreacted chlorine gas by using an alkaline solution.

8. The method according to claim 7, wherein the alkaline solution is KOH, NaOH, or $NH_4OH$ solution.

9. The method according to claim 3, wherein the temperature is in a range of 70 to 90° C.

10. The method according to claim 5, wherein the temperature is in a range of 50 to 70° C.

11. The method of claim 1, wherein the pressure is about 1.01 atm.

12. The method of claim 2, wherein the pressure is about 1.01 atm.

13. The method of claim 3, wherein the pressure is about 1.01 atm.

14. The method of claim 5, wherein the pressure is about 1.01 atm.

15. The method of claim 6, wherein the pressure is about 1.01 atm.

16. The method of claim 7, wherein the pressure is about 1.01 atm.

* * * * *